US012807644B2

(12) United States Patent
Ji et al.

(10) Patent No.: US 12,807,644 B2
(45) Date of Patent: Nov. 24, 2026

(54) MILK-DERIVED POLYPEPTIDE DERIVATIVE, COMPOSITION AND METHOD FOR PREVENTING AND TREATING OBESITY

(71) Applicant: Nanjing Maternity and Child Health Care Hospital, Nanjing (CN)

(72) Inventors: Chenbo Ji, Nanjing (CN); Xianwei Cui, Nanjing (CN)

(73) Assignee: NANJING MATERNITY AND CHILD HEALTH CARE HOSPITAL, Nanjing (CN)

( * ) Notice: Subject to any disclaimer, the term of this patent is extended or adjusted under 35 U.S.C. 154(b) by 922 days.

(21) Appl. No.: 17/812,138

(22) Filed: Jul. 12, 2022

(65) Prior Publication Data

US 2023/0040594 A1 Feb. 9, 2023

(30) Foreign Application Priority Data

Jul. 13, 2021 (CN) ......................... 202110791272.8

(51) Int. Cl.

*C07K 7/00* (2006.01)
*A23L 33/19* (2016.01)
*A61P 3/04* (2006.01)
*C07K 7/06* (2006.01)
*C07K 7/08* (2006.01)
*A61K 38/00* (2006.01)

(52) U.S. Cl.

CPC ................ *C07K 7/06* (2013.01); *A23L 33/19* (2016.08); *A61P 3/04* (2018.01); *C07K 7/08* (2013.01); *A23V 2002/00* (2013.01); *A61K 38/00* (2013.01)

(58) Field of Classification Search

CPC .............. A61P 3/04; C07K 7/06; A23L 33/19
See application file for complete search history.

(56) References Cited

FOREIGN PATENT DOCUMENTS

| | | | | | |
|---|---|---|---|---|---|
| CN | 113248628 | B | | 10/2021 | |
| JP | 08081388 | A | * | 3/1996 | |
| VN | 10009415 | B | * | 8/2011 | A23L 33/19 |
| WO | WO-0113957 | A2 | * | 3/2001 | A61K 31/155 |
| WO | WO-2015026245 | A1 | * | 2/2015 | A23C 9/00 |
| WO | WO-2016123493 | A1 | * | 6/2016 | A61P 3/06 |
| WO | WO-2016177898 | A1 | * | 11/2016 | A61K 38/1709 |

OTHER PUBLICATIONS

Fardet A, Rock E. In vitro and in vivo antioxidant potential of milks, yoghurts, fermented milks and cheeses: a narrative review of evidence. Nutr Res Rev. Jun. 2018;31(1):52-70. Epub Oct. 2, 2017. (Year: 2017).*

Partial translation of VN-10009415-B (Year: 2011).*

D Kinlen, D Cody, D O'Shea, Complications of obesity, QJM: An International Journal of Medicine, vol. 111, Issue 7, Jul. 2018, pp. 437-443. (Year: 2018).*

Tyagi P, Pechenov S, Anand Subramony J. Oral peptide delivery: Translational challenges due to physiological effects. J Control Release. Oct. 10, 2018;287:167-176. (Year: 2018).*

Chang CJ, Jian DY, Lin MW, Zhao JZ, Ho LT, Juan CC. Evidence in obese children: contribution of hyperlipidemia, obesity-inflammation, and insulin sensitivity. PLoS One. May 26, 2015;10(5):e0125935. (Year: 2015).*

Gupta et al., Identification of antioxidant peptides in cheddar cheese made with adjunct culture *Lactobacillus casei* ssp. *casei* 300, 2010, Milchwissenschaft, vol. 65, No. 4, 396-399. (Year: 2010).*

Dal et al. The Protective Effect of Antioxidants Consumption on Diabetes and Vascular Complications. Diseases. Jul. 11, 2016;4(3): 24. (Year: 2016).*

"Chinese Application No. 202110791272.8, First Office Action dated Aug. 23, 2021", (Aug. 23, 2021), 10 pgs.

"Chinese Application No. 202110791272.8, Notification to Grant Patent Right for Invention dated Sep. 7, 2021", (Sep. 7, 2021), 3 pgs.

Fardet, Anthony, et al., "In vitro and in vivo antioxidant potential of milks, yoghurts, fermented milks and cheeses: a narrative review of evidence", Nutrition Research Reviews (2018), 31, 52-70, (2018), 52-70.

Li, Yao-Wang, et al., "Structure—activity relationship study of antioxidative peptides by QSAR modeling: the amino acid next to C-terminus affects the activity", Journal of Peptide Science, vol. 17, Issue 6 [abstract only], (Apr. 14, 2011), 454-462.

Rival, Sandrine G., et al., "Caseins and Casein Hydrolysates. 2. Antioxidative Properties and Relevance to Lipoxygenase Inhibition", J. Agric. Food Chem. 2001, 49, 295-302, (Dec. 1, 2000), 295-302.

* cited by examiner

*Primary Examiner* — Melissa L Fisher
*Assistant Examiner* — Sara E Konopelski Snavely
(74) *Attorney, Agent, or Firm* — MUNCY, GEISSLER, OLDS & LOWE, P.C.

(57) ABSTRACT

The present invention includes a milk-derived polypeptide derivative, composition and its method for using. The milk-derived polypeptide together with its cell penetrating peptide derivatives can slow down body weight gain of mice induced by high-fat diet, reduce blood glucose, serum triglycerides and insulin levels, and improve insulin sensitivity and glucose tolerance. In addition, it can function to reduce body weight and blood glucose of already established obese mice model. Therefore, it has potentials to prepare drugs, health care products and food additives for preventing and treating obesity and its complications and other related diseases.

2 Claims, 4 Drawing Sheets

Specification includes a Sequence Listing.

MILK-DERIVED POLYPEPTIDE DERIVATIVE, COMPOSITION AND METHOD FOR PREVENTING AND TREATING OBESITY

CROSS REFERENCE TO RELATED APPLICATION

This Non-provisional application claims priority under 35 U.S.C. § 119(a) to Chinese Patent Application No. 202110791272.8, filed on 13 Jul. 2021, the entire contents of which is hereby incorporated by reference in its entirety.

INCORPORATION BY REFERENCE OF SEQUENCE LISTING PROVIDED AS AN XML FILE

A Sequence Listing is provided herewith as an xml file, "2253463.xml" created on Jul. 11, 2022 and having a size of 8,192 bytes. The content of the xml file is incorporated by reference herein in its entirety.

TECHNICAL FIELD

The present invention relates to the field of polypeptide and cell metabolism, in particular to a milk-derived polypeptide derivative, composition and method for using in preventing and treating obesity and its complications treating.

BACKGROUND ART

Obesity is a chronic nutritional disease, but the harm is very huge, which not only seriously affects physical and psychological health, but also causes complications such as Type 2 diabetes, cardiovascular diseases and hypertension. Theoretically, the obesity is due to the fact that long-term energy intake of the body exceeds energy consumption, and excessive energy is stored in the adipocytes, resulting in excessive body fat content. However, in real life, an obesity treatment strategy of promoting energy consumption by exercises and reducing energy intake by diet control presents little effect because it is difficult for most of obese patients to adhere thereto. Although surgical treatments may improve symptoms of obesity, it is generally not an option unless the obesity is very serious. Due to the lack of effective means for preventing and treating obesity, the number of obese people rapidly grows in the world, and obesity has become a serious global public health problem. Therefore, it is urgent to actively seek effective obesity treatment methods.

There are two main kinds of adipose tissue in human and other mammals: white adipose tissue (iWAT) and brown adipose tissue (BAT). However, the white adipose tissue can undergo a browning change when stimulated by external factors (such as cold, β-adrenergic receptor agonist, etc.), resulting in a new kind of fat cells: beige fat cells, which are called thermogenic fat cells together with the brown fat cells. Although the brown fat cells and the beige fat cells originate differently, they have a similar characteristic, that is, they can release lipids in a form of heat through mitochondrial uncoupling protein 1 (UCP1). This characteristic not only helps newborns preserving heat, but also provides a new strategy for adult obesity prevention and treatment. It has been proved in human and animal experiments that increased content and activity of thermogenic fat cells can significantly improve carbohydrate metabolism and insulin sensitivity, and alleviate obesity and insulin resistance caused by high-fat diet or gene defects. The BAT content is negatively correlated with the body mass index, and about 40-50 g of active BAT can metabolized to 20% of daily energy intake. Therefore, a new way is expected to be provided for prevention and treatment of adult obesity from the perspective of increasing the content and activity of the thermogenic fat cells in a human body.

Polypeptides are a kind of compounds with unique biological activities formed by linking 2-50 amino acids by peptide bonds. Polypeptides have advantages of low molecular weight, high activity per unit mass, difficult in vivo accumulation, easy synthesis and modification as good molecular basis for drug development, becoming a hot spot in researches and development of new drugs in recent years. At present, many new polypeptides have been reported in researches of obesity prevention and treatment, such as tripeptide (VPP, valyl prolyl proline) from milk casein, which can improve insulin resistance caused by high-fat feeding and reduce inflammatory reaction of adipose tissues through drinking water intake; the erythropoietin (EPO) derived peptides, which can not only have the effects of inhibiting differentiation of adipocytes and secretion of inflammatory factors of mice, but also significantly prevent the obesity and improve the insulin resistance of high-fat-fed mice after intraperitoneal injection. With successful marketing of glucagon-like peptide 1 (GLP-1) receptor agonists for treatment of diabetes, and powerful regulatory activity of polypeptides in obesity prevention and treatment, polypeptide drugs will surely become one of important breakthroughs in effective prevention and treatment of the obesity.

Peptide sequence VKEAMAPK shown as SEQ ID NO: 1 is a polypeptide which is generally present in raw milk and dairy products, it is obtained from fracture of β-casein 98-105 amino acids. It is shown in previous studies that VKEAMAPK SEQ ID NO: 1 has antioxidant activity, that is, it can scavenge free radicals produced in vivo. Recent studies also have found that VKEAMAPK SEQ ID NO: 1 can also be detected in human milk, suggesting that puerpera can be promoted to pass VKEAMAPK SEQ ID NO: 1 ingested through the milk can be passed to fetus through breast feeding.

SUMMARY

The object of the present disclosure is to provide an isolated milk-derived polypeptide sequence, and a milk-derived polypeptide derivative formed by connecting its N-terminal with a cell penetrating sequence; another object of the present disclosure is to provide a composition containing the aforementioned milk-derived polypeptide derivatives; another object of the present disclosure is to provide the method for preventing and treating obesity and obesity complications with the aforementioned milk-derived polypeptide derivative.

In order to achieve above-mentioned objects of the disclosure, a milk-derived polypeptide derivative of the present disclosure includes an active amino acid sequence VKEAMAPK shown as SEQ ID NO: 1. This segment of polypeptide sequence is discovered to achieve effects of reducing weight and lowering blood glucose by activating metabolic activity of thermogenic fat, showing its potential as a drug for obesity prevention and treatment. So far, there is no report about VKEAMAPK SEQ ID NO: 1 in obesity prevention and treatment. , and this is highly innovative in application. On a basis of the aforementioned milk-derived polypeptide, the present disclosure further provides its derivatives, which, specifically, includes an active amino acid sequence of SEQ ID NO: 1 and a cell penetrating amino acid sequence. The cell penetrating amino acid sequence is located at N-terminal of the active amino acid sequence. The milk-derived polypeptide and its derivative can be obtained by amplification and expression with biotechnologies, or by a chemical synthesis method (such as a solid phase/liquid phase synthesis method).

Generally, the polypeptide derivative is a peptide chain consisting of preferably 18-25 amino acids, so the length of the cell penetrating amino acid sequence is preferably 10-17 amino acids, and the milk-derived polypeptide derivative should be a linear peptide chain, which can be obtained by a conventional chemical modification method or gene modification method.

Preferably, the cell penetrating amino acid sequence of the polypeptide derivative comprises at least one segment of oligo-arginine sequence, and a number of arginine in the cell penetrating amino acid sequence is no lower than 40%. More preferably, the N-terminal of the active amino acid sequence is sequentially connected with oligomeric amino acid fragments of glutamine and proline. Cell penetrating amino acid sequences formed by these oligomeric amino acids can effectively connect the active sequence, transport across a cell membrane efficiently without triggering other reactions. The oligo-arginine sequence refers to a sequence combined and formed by at least two adjacent arginine.

More specifically, the polypeptide derivative may be following amino acid sequences:

```
SEQ ID NO: 2: GRKKRRQRRRVKEAMAPK,

SEQ ID NO: 3: CYGRKKRRQRRRVKEAMAPK,

SEQ ID NO: 4: GRKKRRQRRRPPQVKEAMAPK,

SEQ ID NO: 5: GRKKRRQRRRPPQQVKEAMAPK.
```

The preferred sequences are SEQ ID NO: 4 and SEQ ID NO: 5, and the most preferred solution is with an amino acid sequence shown in SEQ ID NO: 5.

A composition is further provided in the present disclosure, which includes any one or more of the aforementioned milk-derived polypeptide derivatives, and a pharmaceutically acceptable carrier or excipient.

The aforementioned milk-derived polypeptide and its derivative or composition can be prepared as drugs for preventing and treating obesity and/or obesity complications, or health care products or food additives for preventing obesity and/or obesity complications, so as to achieve effects of controlling body weight increasing and reducing fasting blood glucose. The obesity complications include hyperglycemia and/or hyperlipidemia. Specifically, the body weight increasing can be controlled effectively, and the body weight increasing (weight increasing of white adipose tissues) of a test subject is significantly reduced in a model test for an obese animal obtained by feeding high-fat food; and insulin sensitivity and glucose tolerance of the obese animal can be obviously enhanced, and a fasting blood glucose level, a blood lipid level and an insulin level of the obese animal are further reduced. Meanwhile, results of H&E staining and UCP1 protein immunohistochemistry studies showed that the milk-derived polypeptide can serve to reduce lipid accumulation in the adipose tissues induced by high-fat diet, and this reduction is achieved by increasing thermogenic activity of the adipose tissues, so the milk-derived polypeptide and its derivatives had effect of treating obesity.

The polypeptide derivative can be administrated at a concentration to exerting biological activity of 5-10 mg/Kg. With a dose of 5 mg/Kg, the polypeptide derivative can initially possess the biological activity, and with a dose of 10 mg/Kg, a more significant effect can be achieved for the biological activity.

DETAILED DESCRIPTION

Figure 1:
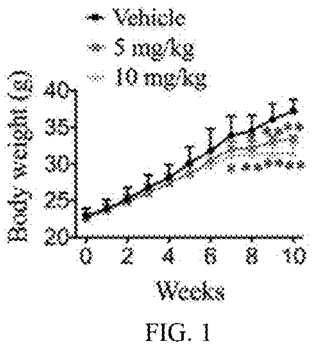
FIG. 1 is a graph of different concentrations of milk-derived polypeptide derivatives in Embodiment 2 on body weight gain of mice with high-fat diet, SEQ ID NO. 5 is the peptide used in Embodiments 2.
Figure 2:
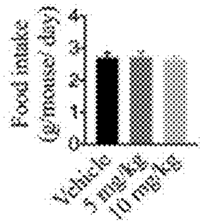
FIG. 2 is a bar chart illustrating different concentrations of milk-derived polypeptide derivatives in Embodiment 2 on food intake of mice with high-fat diet, SEQ ID NO. 5 is the peptide used in Embodiments 2.

The present disclosure will be further explained below with reference to the drawings and specific Embodiments.

Embodiment 1

Unless otherwise specified, peptide chains in the following embodiments of the disclosure were obtained from chemical synthesis by Shanghai Ketai Biological Co., Ltd., with purity of more than 98%.

An isolated linear milk-derived polypeptide is provided in this embodiment, which is a amino acid sequence shown in SEQ ID NO.1: Val-Lys-Glu-Ala-Met-Ala-Pro-Lys.

A derivative of this milk-derived polypeptide is further provided in this embodiment, with its N-terminal being connected to a cell penetrating sequence to form a linear nucleotide sequence of 18-25 amino acids in length: SEQ ID NO.2: GRKKRRQRRRVKEAMAPK, with a molecular formula of $C_{93}H_{175}N_{41}O_{22}S$, an average molecular weight of 2251.7 g/mol, and an average isoelectric pH of 12.471.

SEQ ID NO.3: CYGRKKRRQRRRVKEAMAPK, with a molecular formula of $C_{108}H_{197}N_{45}O_{26}S$, an average molecular weight of 2574.06 g/mol, and an average isoelectric pH of 12.471.

SEQ ID NO.4: GRKKRRQRRRPPQVKEAMAPK, with a molecular formula of $C_{105}H_{189}N_{43}O_{25}S_2$, an average molecular weight of 2518.02 g/mol, and an average isoelectric pH of 11.911.

SEQ ID NO.5: GRKKRRQRRRPPQQVKEAMAPK, with a molecular formula of $C_{113}H_{205}N_{47}O_{28}S$, an average molecular weight of 2702.19 g/mol, and an average isoelectric pH of 12.471.

Combination of any one or more of the above amino acid sequences SEQ ID NO.2 to SEQ ID NO.5 as an active ingredient can be prepared into a composition for prevention and treatment of obesity and obesity complications by adding other pharmaceutically acceptable carriers or excipients.

Necessary modifications can be made by those skilled in the art without departing from protection scope of the present disclosure, including but not limited to protection/de-protection of specific groups, acylation, alkylation, amidation, esterification of a C-terminal and/or an N-terminal and/or a side chain, and other special coupling or chelating modifications.

Embodiment 2 Effect of Milk-Derived Polypeptide on Weight Increasing of Animal Model with High-Fat Diet 1. Experimental Method C57BL/6J male mice at 6-8 weeks old were used as research subjects, and an experiment was carried out after adaptation to a SPF animal room for one week. The mice were fed with high-fat diet (with 60% of fat content) for 10 weeks to induce obesity phenotype in mice. At the same time, different drug concentrations (5 mg/kg and 10 mg/kg) were provided, and the milk-derived polypeptide derivatives corresponding to SEQ ID NO.5 were administered by intraperitoneal injection twice a week, with dissolved normal saline (Vehicle) as a control. The mice are weighed to obtain body weight and their food intake calculated every week. After the mice were killed, brown fat (BAT) at scapular, inguinal white adipose tissue (iWAT) and epididymal white adipose tissue (eWAT) were photographed, weighed to obtain wet weight and lean mass of the mice was calculated.

Experimental Results

Figure 3:
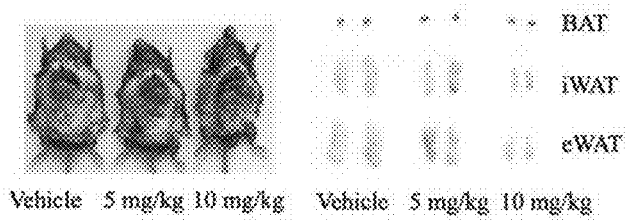
FIG. 3 illustrates different concentrations of milk-derived polypeptide derivatives in Embodiment 2 on adipose tissues of various parts of mice with high-fat diet, SEQ ID NO. 5 is the peptide used in Embodiments 2.
Figure 4:
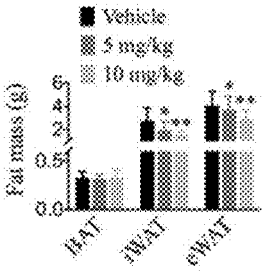
FIG. 4 is a bar chart of different concentrations of milk-derived polypeptide derivatives in Embodiment 2 on wet weight of fat of mice with high-fat diet, SEQ ID NO. 5 is the peptide used in Embodiments 2.
Figure 5:
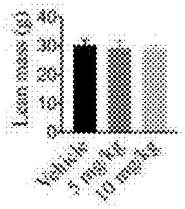
FIG. 5 is a bar chart of different concentrations of milk-derived polypeptide derivatives in Embodiment 2 on lean mass of mice with high-fat diet, SEQ ID NO. 5 is the peptide used in Embodiments 2.

Referring to FIG. 1 to FIG. 5, Compared with the control group (Vehicle), weight growth of the mice in a 5 mg/kg group started to slow down at a 8th week, while that of the mice in a 10 mg/kg group started to slow down at a 7th week. By a 10th week, weight of the mice in a milk-derived polypeptide derivative intervention group was significantly lower than that in the control group (Vehicle). After dissection, respective adipose tissues were photographed as shown in FIG. 3. Volumes of subcutaneous and abdominal white adipose tissues in the milk-derived polypeptide derivative intervention group decreased significantly. It is found in a wet weight test of the adipose tissues as shown in FIG. 4 that fat content of the mice in the milk-derived polypeptide derivative intervention group decreased significantly, while FIG. 5 showed that there was no significant change in the lean mass of the mice. The above indicates that the milk-derived polypeptide and its derivative can slow down obesity weight increasing induced by high-fat diet, which is caused by decrease of body fat content, and thus functions to prevent obesity.

Embodiment 3 Effect of Milk-Derived Polypeptide on Insulin Sensitivity and Glucose Tolerance of Animal Model with High-Fat Diet 1. Experimental Method C57BL/6J male mice at 6-8 weeks old were used as research subjects, and an experiment was carried out after adaptation to a SPF animal room for one week. The mice were fed with high-fat diet (with 60% of fat content) for 10 weeks to induce obesity phenotype in mice. At the same time, different drug concentrations (5 mg/kg and 10 mg/kg) of the milk-derived polypeptide derivatives corresponding to SEQ ID NO.5 were provided, and were administered by intraperitoneal injection twice a week, with dissolved normal saline (Vehicle) as a control.

Insulin Sensitivity: The mice are fasted overnight for 12 hours, and at a next day, insulin was injected by intraperitoneal injection at a standard of 0.75 U per kg of weight. Blood samples were taken from tail vein at 0 min, 15 min, 30 min, 60 min, 90 min and 120 min after the injection, and changes of the blood glucose in the mice were measured by a blood glucose meter to evaluate the insulin sensitivity of the mice. Glucose tolerance test: after fasting for 6 hours, the mice were injected with glucose by intraperitoneal injection at a concentration of 1 g per kg of weight. Blood samples were taken from tail vein at 0 min, 15 min, 30 min, 60 min, 90 min and 120 min after the injection, and changes of the blood glucose in the mice were measured by a blood glucose meter to evaluate the glucose tolerance of the mice.

Experimental Results

Figure 6:
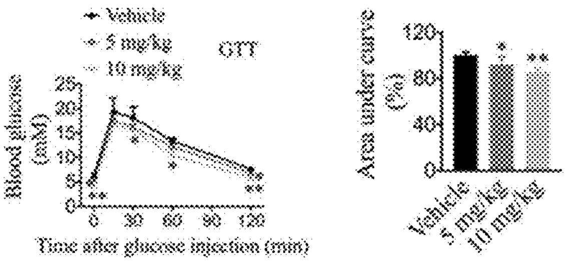
FIG. 6 is a graph of different concentrations of milk-derived polypeptide derivatives in Embodiment 3 on glucose tolerance (GTT) of mice with high-fat diet, SEQ ID NO. 5 is the peptide used in Embodiments 3.

FIG. 6 shows effects of different concentrations of milk-derived polypeptide derivatives on the glucose tolerance (GTT) in the obese mice. It can be seen that after continuous intervention for 10 weeks with the milk-derived polypeptide derivatives, fasting blood glucose levels of the mice were lower than those of the control group within 2 hours after glucose or insulin injection, and a curve of blood glucose rise was well controlled. After the intervention of 10 mg/kg concentration for 10 weeks, an area under the curve had significant statistical significance. It can be expected that intaking the milk-derived polypeptide derivative with a certain concentration for a long time helps to improve glucose tolerance of an individual, and provides corresponding drugs, health care products and food additives for prevention and treatment of obesity and its complications as active ingredients.

Figure 7:
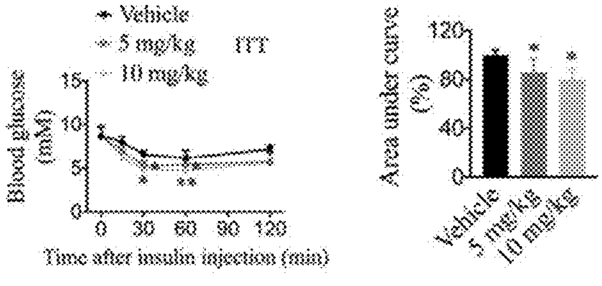
FIG. 7 is a graph of different concentrations of milk-derived polypeptide derivatives in Embodiment 3 on insulin sensitivity (ITT) of mice with high-fat diet, SEQ ID NO. 5 is the peptide used in Embodiments 3.

Similarly, FIG. 7 shows effects of different concentrations of milk-derived polypeptide derivatives on insulin sensitivity (ITT) in the obese mice. When an intake concentration is 5 mg/kg, it presents certain statistical significance, so it can be combined with prevention and treatment of hyperglycemia or diabetes to further improve the effects.

Embodiment 4 Effect of Milk-Derived Polypeptide on Blood Glucose, Blood Lipid and Insulin Levels of Animal Model with High-Fat Diet 1. Experimental Method C57BL/6J male mice at 6-8 weeks old were used as research subjects, and an experiment was carried out after adaptation to a SPF animal room for one week. The mice were fed with high-fat diet (with 60% of fat content) for 10 weeks to induce obesity phenotype in mice. At the same time, different drug concentrations (5 mg/kg and 10 mg/kg) of the milk-derived polypeptide derivatives corresponding to SEQ ID NO.5 were provided, and were administered by intraperitoneal injection twice a week, with resolvent saline (Vehicle) as a control. The changes of the blood glucose in the mice were detected by a Roche blood glucose meter, and changes of blood lipid and insulin level in the mice were detected by Applygen and Millipore commercial kits respectively.

Experimental Results

Figure 8:
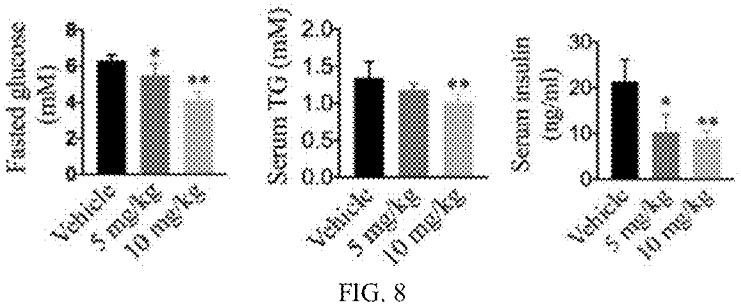
FIG. 8 is a bar chart showing changes of fasting blood glucose, triglyceride and insulin levels of mice with high-fat diet after intervention of different concentrations of milk-derived polypeptide derivatives in Embodiment 4, SEQ ID NO. 5 is the peptide used in Embodiments 4.

FIG. 8 shows that after continuous intervention for 10 weeks, the fasting blood glucose, blood lipid and insulin levels of the mice were significantly reduced. Therefore, the milk-derived polypeptide derivative is used for preventing and treating obesity complications such as hyperglycemia and hyperlipidemia.

Embodiment 5 Effect of Milk-Derived Polypeptide on Morphology and Thermogenic Activity of Brown Fat and White Fat Droplets in Animal Model with High-Fat Diet 1. Experimental Method C57BL/6J male mice at 6-8 weeks old were used as research subjects, and an experiment was carried out after adaptation to a SPF animal room for one week. The mice were fed with high-fat diet (with 60% of fat content) for 10 weeks to induce obesity phenotype in mice. At the same time, different drug concentrations (5 mg/kg and 10 mg/kg) were provided, and the milk-derived polypeptide derivatives corresponding to SEQ ID NO.5 were administered by intraperitoneal injection twice a week, with dissolved normal saline (Vehicle) as a control. After 10 weeks of intervention, the mice were killed, and brown fat (BAT) at scapula and inguinal subcutaneous white adipose tissues (iWAT) were taken to be fixed with a adipose tissue fixing solution (Solarbio, G2185) for 24 hours. H&E staining and a UCP1 protein immunohistochemistry study were carried out after dehydration, paraffin embedding and sectioning. The H&E staining is performed using a kit (ab245800) from Abcam, and specific steps can be found in kit instructions. Tissue sections were subjected to the immunohistochemistry study after dewaxing and antigen repairing. Specifically, the sections were incubated overnight with UCP1 antibody (1:200, Proteintech) at 4 degrees. The antibody was diluted with PBS containing 1% of BSA, and a color reaction was carried out next day with a DAB kit from Abcam. Specific operations can be referred to kit experimental steps. At the same time, total protein was extracted by a RIPA lysate, and expression of the UCP1 protein in the adipose tissues was detected by a Western blot method after quantifying, SDS-PAGE electrophoresis and transmembrane.

Experimental Results

Figure 9:
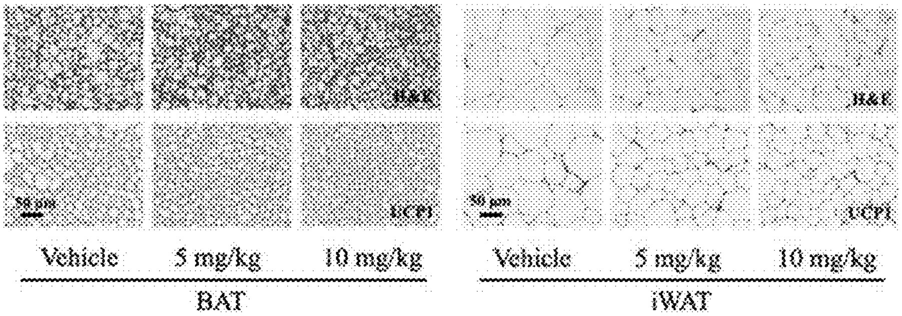
FIG. 9 is a diagram showing H&E staining and UCP1 protein immunohistochemistry of adipose tissues of mice with high-fat diet after intervention of different concentrations of milk- derived polypeptide derivatives in Embodiment 5, SEQ ID NO. 5 is the peptide used in Embodiments 5.
Figure 10:
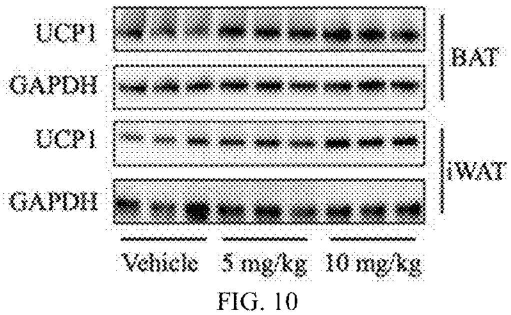
FIG. 10 is a Western blot test chart of UCP1 protein in adipose tissues of mice with high- fat diet after intervention of different concentrations of milk-derived polypeptide derivatives in Embodiment 5, SEQ ID NO. 5 is the peptide used in Embodiments 5.

As shown in FIG. 9, H&E staining results show that morphology sizes (white pore sizes) of lipid droplets in brown fat and white adipose tissues are significantly reduced, indicating that lipid accumulation in the adipose tissues is reduced and obesity performance is significantly improved. It is shown in UCP1 immunohistochemistry results that brown areas in both brown and white adipose tissues were significantly increased under action of the milk-derived polypeptide derivatives, suggesting that expression of the UCP1 protein was significantly increased and metabolic capacity of the adipose tissues was enhanced. Western blot results in FIG. 10 show that contents of the UCP1 protein in brown and white adipose tissues are also significantly increased, and it shows a certain dose-dependent relationship and a good effect can be provided at a low (5 mg/Kg) drug concentration. The above indicates that the milk-derived polypeptide and its derivative can serve to reduce lipid accumulation in the adipose tissues induced by high-fat diet, and this reduction is achieved by increasing thermogenic activity of the adipose tissues.

Embodiment 6 Effect of Milk-Derived Polypeptide on Body Weight and Blood Glucose of Obese Animal Model 1. Experimental Method C57BL/6J male mice at 6-8 weeks old were used as research subjects, and an experiment was carried out after adaptation to a SPF animal room for one week. The mice were fed with high-fat diet (with 60% of fat content) for six months to induce obesity phenotype in mice. After six months, the milk-derived polypeptide derivative shown by SEQ ID NO.5 (10 mg/kg) was administered by intraperitoneal injection once a day and continuously for 8 weeks. The mice were weighed every week for their weight changes, and at the same time, blood glucose changes of the mice were detected by a blood glucose meter. After intervention, the mice were killed, and then brown fat (BAT) at scapular, inguinal white adipose tissue (iWAT) and epididymal white adipose tissue (eWAT) were photographed. As mentioned above, H&E staining was also performed to observe morphological changes of lipid droplets, and expression of the UCP1 protein in adipose tissues was detected by immunohistochemistry and the Western blot methods.

Experimental Results

Figure 11:
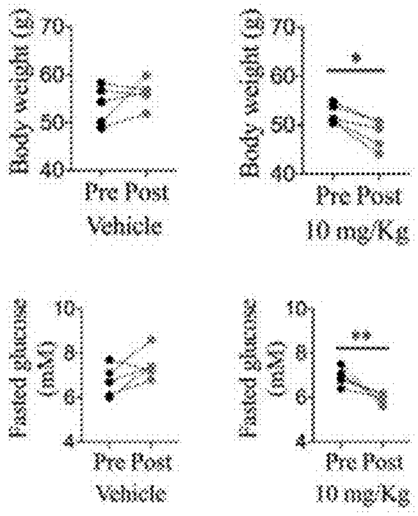
FIG. 11 shows change of body weight and a fasting blood glucose level of obese model mice after intervention of milk-derived polypeptide derivatives in Embodiment 6 compared with a control group.
Figure 12:
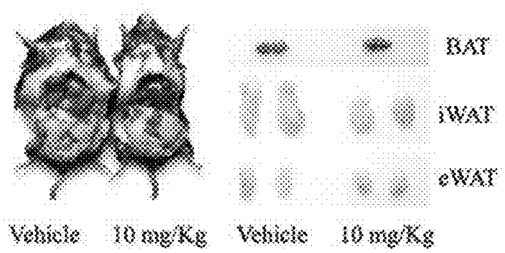
FIG. 12 is an anatomy of adipose tissues of various parts of obese model mice after intervention of milk-derived polypeptide derivatives in Embodiment 6 compared with a control group.
Figure 13:
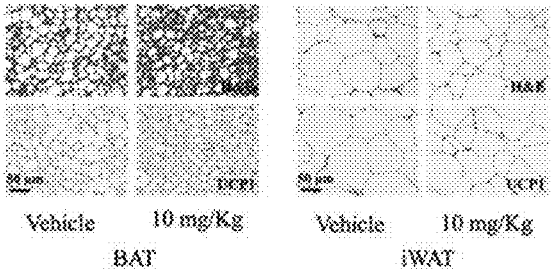
FIG. 13 a diagram showing H&E staining and UCP1 protein immunohistochemistry of adipose tissues from obese model mice after intervention of milk-derived polypeptide derivatives in Embodiment 6 compared with a control group.
Figure 14:
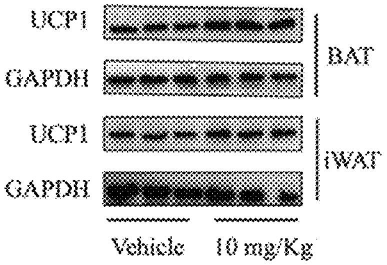
FIG. 14 is a Western blot test chart of UCP1 protein in adipose tissues of obese model mice after intervention of milk-derived polypeptide derivatives in Embodiment 6 compared with a control group.

As shown in FIG. 11, body weight of the obese mice induced by the high-fat diet can be significantly reduced after 8 weeks of administration of the milk-derived polypeptide derivatives, while weight of the control group has no significant change. In addition, fasting blood glucose of the mice in an administration group decreased, thus achieving effects of reducing the weight and reducing the blood glucose. After dissection, morphological observation shows that tissue volumes of white fat (subcutaneous and abdominal) and brown fat (scapular areas) in various parts are significantly reduced, suggesting that lipid accumulation is reduced. The results are shown in FIG. 12. The H&E staining also shows that sizes of the lipid droplets in the two tissues decreased significantly, which also indicated that lipid accumulation is decreased. The immunohistochemistry and the Western blot test in FIG. 13 and FIG. 14 indicate that the expression of UCP1 was increased in two kinds of adipose tissues. Details can be referred to brown areas in FIG. 13 and band thicknesses in FIG. 14. The above results show that this therapeutic effect is also achieved by activating the thermogenic activity of the adipose tissues and thus reducing lipid accumulation in the adipose tissues.

What is claimed is:

1. A method for treating obesity with a milk-derived polypeptide derivative comprising an active amino acid sequence of SEQ ID NO: 2, SEQ ID NO: 3, SEQ ID NO: 4 or SEQ ID NO: 5, comprising administrating the polypeptide derivative at 5-10 mg/Kg of a body weight of a subject in need thereof.

2. The method according to claim 1, wherein the milk-derived polypeptide derivative is mixed with at least a pharmaceutically acceptable carrier or excipient.

* * * * *

SEQUENCE LISTING

```
Sequence total quantity: 5
SEQ ID NO: 1            moltype = AA  length = 8
FEATURE                 Location/Qualifiers
source                  1..8
                        mol_type = protein
                        organism = synthetic construct
SEQUENCE: 1
VKEAMAPK                                                    8

SEQ ID NO: 2            moltype = AA  length = 18
FEATURE                 Location/Qualifiers
source                  1..18
                        mol_type = protein
                        organism = synthetic construct
SEQUENCE: 2
GRKKRRQRRR VKEAMAPK                                         18

SEQ ID NO: 3            moltype = AA  length = 20
FEATURE                 Location/Qualifiers
source                  1..20
                        mol_type = protein
                        organism = synthetic construct
SEQUENCE: 3
CYGRKKRRQR RRVKEAMAPK                                       20

SEQ ID NO: 4            moltype = AA  length = 21
FEATURE                 Location/Qualifiers
source                  1..21
                        mol_type = protein
                        organism = synthetic construct
SEQUENCE: 4
GRKKRRQRRR PPQVKEAMAP K                                     21

SEQ ID NO: 5            moltype = AA  length = 22
FEATURE                 Location/Qualifiers
source                  1..22
                        mol_type = protein
                        organism = synthetic construct
SEQUENCE: 5
GRKKRRQRRR PPQQVKEAMA PK                                    22
```